(12) United States Patent
Miyazaki

(10) Patent No.: US 9,107,589 B2
(45) Date of Patent: Aug. 18, 2015

(54) MAGNETIC RESONANCE IMAGING APPARATUS AND MAGNETIC RESONANCE IMAGING METHOD

(71) Applicant: Mitsue Miyazaki, Des Plaines, IL (US)

(72) Inventor: Mitsue Miyazaki, Des Plaines, IL (US)

(73) Assignees: KABUSHIKI KAISHA TOSHIBA, Tokyo (JP); TOSHIBA MEDICAL SYSTEMS CORPORATION, Otawara-Shi, Tochigi (JP)

( * ) Notice: Subject to any disclaimer, the term of this patent is extended or adjusted under 35 U.S.C. 154(b) by 190 days.

(21) Appl. No.: 13/644,338

(22) Filed: Oct. 4, 2012

(65) Prior Publication Data

US 2013/0096419 A1   Apr. 18, 2013

Related U.S. Application Data

(63) Continuation-in-part of application No. 12/923,894, filed on Oct. 13, 2010.

(30) Foreign Application Priority Data

Oct. 13, 2011   (JP) .................................. 2011-226159

(51) Int. Cl.
*A61B 5/05* (2006.01)
*A61B 5/026* (2006.01)
(Continued)

(52) U.S. Cl.
CPC ............. *A61B 5/0263* (2013.01); *A61B 5/0044* (2013.01); *A61B 5/029* (2013.01); *A61B 5/055* (2013.01); *G01R 33/56308* (2013.01); *A61B 5/024* (2013.01); *G01R 33/4838* (2013.01); *G01R 33/5635* (2013.01)

(58) Field of Classification Search
CPC ............................. A61B 5/0263; A61B 5/055
USPC ........................... 600/407, 410–423; 382/128
See application file for complete search history.

(56) References Cited

U.S. PATENT DOCUMENTS 5,315,248 A   5/1994  Yamaguchi
5,684,398 A   11/1997  Takiguchi et al.
(Continued)

FOREIGN PATENT DOCUMENTS

CN   101444419 A   6/2009
JP   1-238851   9/1989
(Continued)

OTHER PUBLICATIONS

Amendment Under 37 C.F.R. § 1.111 in response to Office Action in U.S. Appl. No. 12/923,894, Miyazaki, submitted on Apr. 11, 2013.
(Continued)

*Primary Examiner* — James Kish
(74) *Attorney, Agent, or Firm* — Nixon & Vanderhye P.C.

(57) ABSTRACT

A magnetic resonance imaging apparatus includes a collecting unit, a specifying unit, an acquiring unit and a calculating unit. The collecting unit collects a plurality of fluid images that are images of a fluid traveling though a subject. The specifying unit specifies a distance traveled by the fluid by using a difference image between a reference image that is one of the fluid images and each fluid image. The acquiring unit acquires an elapsed time corresponding to the traveled distance from pulse sequence information that is used to collect the fluid images. The calculating unit calculates a flow velocity of the fluid by dividing the traveled distance by the elapsed time.

15 Claims, 9 Drawing Sheets

(51) Int. Cl.
*A61B 5/055* (2006.01)
*A61B 5/00* (2006.01)
*A61B 5/029* (2006.01)
*G01R 33/563* (2006.01)
*G01R 33/483* (2006.01)
*A61B 5/024* (2006.01)

(56) References Cited

U.S. PATENT DOCUMENTS

| | | | |
|---|---|---|---|
| 6,760,611 | B1 | 7/2004 | Watanabe |
| 6,801,800 | B2 | 10/2004 | Miyazaki et al. |
| 2008/0061780 | A1 | 3/2008 | Yamada et al. |
| 2008/0161678 | A1 | 7/2008 | Miyazaki et al. |
| 2009/0143667 | A1 | 6/2009 | Kovacs et al. |
| 2009/0148020 | A1 | 6/2009 | Sugiura |
| 2009/0245607 | A1* | 10/2009 | Sugiura .................. 382/131 |
| 2009/0309592 | A1 | 12/2009 | Furudate |
| 2010/0198053 | A1 | 8/2010 | Miyazaki et al. |

FOREIGN PATENT DOCUMENTS

| | | |
|---|---|---|
| JP | 2-255124 | 10/1990 |
| JP | 6-022934 | 2/1994 |
| JP | 7-116143 | 5/1995 |
| JP | 2004-329614 | 11/2004 |
| JP | 2008-23317 | 2/2008 |
| JP | 2009-247773 | 10/2009 |
| JP | 2010-022813 | 2/2010 |
| JP | 2010-051835 | 3/2010 |
| JP | 2010-201154 | 9/2010 |
| JP | 2010-201184 | 9/2010 |

OTHER PUBLICATIONS

Miyazaki et al. "A Novel MR Angiography Technique: Speed Acquisition Using Half-Fourier RARE", 1998.

Miyazaki, et al., "Non-contrast-enhanced MR angiography using 3D ECG-synchronized half-Fourier fast spin echo," *JMRI* 12:776-783 (2000).

Suga, et al., Lung perfusion impairments in pulmonary embolic and airway obstruction with noncontrast MR imaging, *J Appl Physiol* 92:2439-2451 (2002).

Takahashi, et al., "Non-contrast-enhanced renal MRA using time-spatial labeling pulse (t-SLIP) with 3D balanced SSFP," presented at the ISMRM 15$^{th}$ Annual Meeting, Berlin, Germany, p. 179 (2007).

Yamamoto, et al., "Non-contrast-enhanced MRDSM of peripheral arteries using continuous acquisitions of ECG-triggered 2D half-Fourier FSE within a cardiac cycle," presented at the ISMRM 12$^{th}$ Annual Meeting, Toronto, Canada, p. 1709 (2003).

Kanazawa, et al., "Time-spatial labeling inversion tag (t-SLIT) using a selective IR-tag on/off pulse in 2D and 3D half-Fourier FSE as arterial spin labeling," presented at the ISMRM 10$^{th}$ Annual Meeting, Hawaii, p. 140 (2002).

Furudate, et al., "FBI-Navi for Easy Determination of Diastolic and Systolic Triggering Phases in Non-Contrast Fresh Blood Imaging (FBI)," ISMRM 16$^{th}$ Annual Meeting, Toronto, Canada, p. 2902 (2008).

Office Action in U.S. Appl. No. 12/923,894, Miyazaki, mailed Dec. 11, 2012.

Office Action mailed Dec. 9, 2013 in CN 201180003249.2.

Extended European Search Report dated Mar. 12, 2015 in EP 11832599.2.

Zhang H. L. et al., "Body Magnetic Resonance Angiography," Seminars in Roentgenology, W.B. Saunders, US, vol. 44, No. 2, Apr. 1, 2009, pp. 84-98, XP026017913, ISSN: 0037-198X.

* cited by examiner

MAGNETIC RESONANCE IMAGING APPARATUS AND MAGNETIC RESONANCE IMAGING METHOD

CROSS-REFERENCE TO RELATED APPLICATIONS

This application is a continuation-in-part (CIP) of application Ser. No. 12/923,894 filed on Oct. 13, 2010, the entire content of which is hereby incorporated by reference in this application. This application is based upon and claims the benefit of priority from Japanese Patent Application No. 2011-226159, filed on Oct. 13, 2011, the entire contents of all of which is incorporated herein by reference.

FIELD

Exemplary embodiments relate to a magnetic resonance imaging apparatus and a magnetic resonance imaging method.

BACKGROUND

Imaging methods of conventional magnetic resonance imaging apparatuses (hereinafter, MRI (magnetic resonance imaging) system) include a method of imaging a fluid traveling through a subject without using a contrast agent.

DETAILED DESCRIPTION

A magnetic resonance imaging apparatus includes a collecting unit, a specifying unit, an acquiring unit and a calculating unit. The collecting unit collects a plurality of fluid images that are images of a fluid traveling though a subject. The specifying unit specifies a distance traveled by the fluid by using a difference image between a reference image that is one of the fluid images and each fluid image. The acquiring unit acquires an elapsed time corresponding to the traveled distance from pulse sequence information that is used to collect the fluid images. The calculating unit calculates a flow velocity of the fluid by dividing the traveled distance by the elapsed time.

Figure 1:
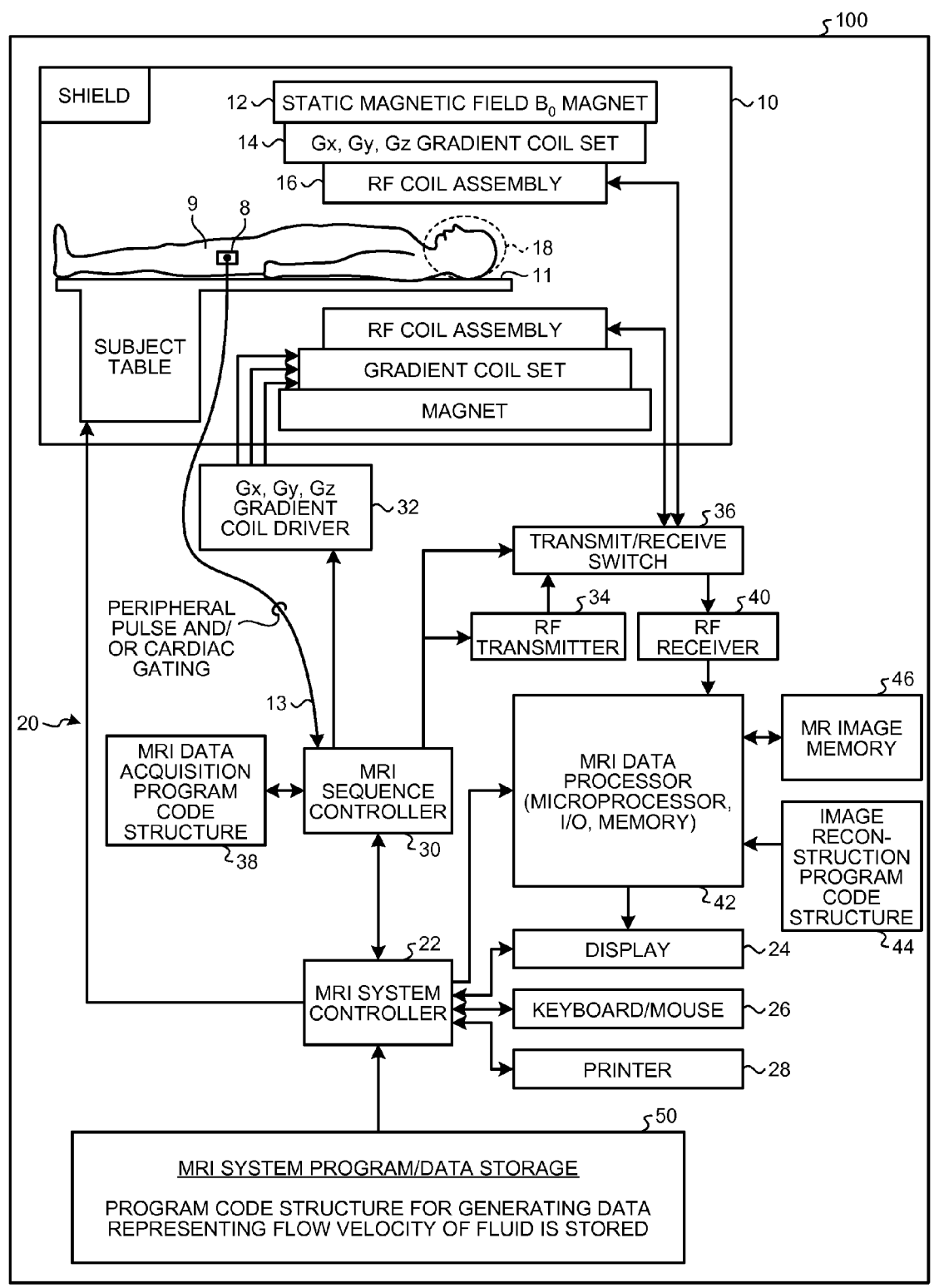
FIG. 1 is a schematic block diagram of an MRI system according to an exemplary embodiment.

An MRI (magnetic resonance imaging) system 100 shown in FIG. 1 includes a gantry 10 (shown in cross-section) and various related system components 20 interfaced therewith. At least the gantry 10 is typically located in a shielded room. One MRI system 100 depicted in FIG. 1 includes a substantially coaxial cylindrical arrangement of a static magnetic field $B_0$ magnet 12, a $G_x$, $G_y$, and $G_z$ gradient coil set 14, and an RF (radio frequency) coil assembly 16. Along the horizontal axis of the components cylindrically arranged, there is an imaging volume 18 shown as encompassing the head of a subject 9 supported by a subject table 11.

An MRI system controller 22 has input/output ports connected to a display 24, a keyboard/mouse 26 and a printer 28. As will be appreciated, the display 24 may be of the touch-screen variety so that it provides control inputs as well.

The MRI system controller 22 interfaces with an MRI sequence controller 30. The MRI sequence controller 30 sequentially controls a $G_x$, $G_y$, and $G_z$ gradient coil drivers 32, as well as an RF transmitter 34 and a transmit/receive switch 36 (if the same RF coil is used for both transmission and reception). The MRI sequence controller 30 includes a suitable program code structure 38 for implementing MRI data acquisition sequences (including the imaging of flowing fluid such as blood) already available in the MRI sequence controller 30. A cardiac signal acquisition apparatus 8 (e.g., ECG (electrocardiogram) or peripheral pulse transducer(s)) coupled appropriately to the body of the subject 9) can output cardiac gating signals 13 serving as signals to trigger the MRI sequence controller 30.

The MRI system 100 includes an RF receiver 40 providing input to an MRI data processor 42 so as to create processed image data to be output to the display 24. The MRI data processor 42 may be also configured to access an image reconstruction program code structure 44 and an MR image memory 46 (e.g., for storing MRI data derived from processing in accordance with the exemplary embodiments and the image reconstruction program code structure 44).

FIG. 1 gives a generalized depiction of an MRI system program/data storage 50. The program code structures (e.g., for image reconstruction and for flow velocity, distance/time measurements, operator inputs, etc.) stored in the MRI system program/data storage 50 is stored in computer-readable storage media accessible to the various data processing components of the MRI system 100. As those in the art will appreciate, the MRI system program/data storage 50 may be segmented and directly connected, at least in part, to various ones of the processing computers of the MRI system 100 having most immediate need for such stored program code structures stored in their normal operation (i.e., rather than being commonly stored and connected directly to the MRI system controller 22).

Indeed, as those in the art will appreciate, the depiction of FIG. 1 is of a very high-level simplified diagram of the typical MRI system 100 with some modifications so as to practice the exemplary embodiments to be described below. The system components can be divided into different logical collections of "boxes" and typically include numerous digital signal processors (DSP (digital signal processors)), microprocessors, special purpose processing circuits (e.g., for fast A/D conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs (central processing unit), registers, buffers, arithmetic units, etc.) progressively change from one clock cycle to another during the operation, the physical state of associated data storage media (e.g., bit storage in magnetic storage media) is transformed from one state to another during operations of such a system. For example, at the conclusion of an MR-imaging reconstruction process, an array of computer-readable accessible data value storage in physical storage media will be transformed from some prior state (e.g., all uniform "zero" values or all "one" values) to a new state. In such a new state, the physical states at the physical sites of such an array vary between minimum and maximum values to represent real world physical events and conditions (e.g., the blood flowing in arteries of a subject over an imaging volume space). As those in the art will appreciate, such arrays of stored data values represent and also constitute a physical structure. In other words, when such an array is sequentially loaded into instruction registers and executed by one or more CPUs of the MRI system 100, a particular sequence of operational states occurs and thus a particular structure of computer control program codes that is transitioned through within the MRI system 100 is constituted.

The exemplary embodiments described below provide improved ways to perform a process of acquiring data including the velocity of the flowing fluid (hereinafter, referred to as "flow velocity" as required) and/or to generate and display MR-images.

There are MR signal strength changes between images collected in synchronism with cardiac systolic and diastolic timings. The MR signal strength changes can be used to obtain a non-contrast time-resolved fluid (e.g., blood) flow by subtracting a systole image with a low signal value from a diastole image with a high signal value and/or subtracting a diastole image with a high signal value from a systole image with a low signal. This is sometimes referred to as time-resolved non-contrast MRA (magnetic resonance angiography). In addition, there are other non-contrast agent imaging techniques for fluid flows such as time-SLIP (time-spatial labeling inversion pulse) sometimes referred to as ASL (arterial spin labeling).

An operator interface to facilitate measuring fluid flow velocities in these non-contrast imaging techniques would be desirable.

In accordance with exemplary embodiments to be described below, fluid flow velocity measurements in non-contrast fluid images can be achieved in at least two ways. The first is a way using diastolic-systolic subtraction images. The MRI system 100 can specify the distance traveled by the fluid by using diastolic-systolic subtraction images. For example, if the artery path is relatively linear, it can be assumed that the path from a start point to an end point is a simple line. Alternatively, even if the artery path is tortuous, the path from a start point to an end point can be specified by connecting strategically placed points along the path. Automatic tracking of distance travelled by the flowing fluid along an arbitrarily-shaped path may also be available. In any event, the distance along which flowing fluid has passed between successive imaging times can be used to calculate specific velocity between successive imaging times, as well as an average or mean velocity over a succession of such imaging times.

The second is a way using a non-contrast Time-SLIP image technique. When a non-contrast Time-SLIP image technique is used, it may involve somewhat different imaging sequences such as FASE (fast asymmetric spin echo) or bSSFP (balanced steady state free precession) in either centric ordering of phase encoding for k-space or sequential ordering of phase encoding for k-space. The numerator is, of course, still the distance travelled by the signal-producing and flowing material (e.g., blood). For Time-SLIP with FASE imaging method, the time increment to be used for the denominator in calculating a flow velocity can be BBTI (black-blood time to inversion) time plus effective time to echo (TEeff). For Time-SLIP with bSSFP, the time increment for the denominator would be BBTI. For Ttime-SLIP with bSSFP in sequential ordering, the time increment for the denominator is BBTI time plus one-half ETL (echo train length) (time corresponding to half of the phase encode number).

Velocity measurements may be made for MR signal producing flow displacements between different ECG (electrocardiogram) (electrocardiogram gating) signal points (for example, systole to diastole) or using FBI (fresh blood imaging)-Navi signal difference plots. Velocity measurement of flowing MR signal displacements or travelled MR signals can be measured.

As just mentioned, displacements of MR signal producing flows using Time-SLIP imaging techniques during BBTI (possibly plus TEeff, and/or ETL/2 depending on k-space ordering) can also be used to calculate a mean velocity.

In an exemplary embodiment, a simple GUI (graphical user interface) may be used (e.g., by depression of a mouse button) to selectively calculate a flow velocity along a travelled distance. The outline of the travelled distance may be depicted by the user (e.g., by defining strategically placed points along the path) or by a system-provided auto-tracking feature. In any event, the distance travelled is then divided by the time interval associated with that distance (e.g., between subtracted images in ECG delayed imaging techniques and/or in Time-SLIP imaging techniques).

The GUI can be used to measure a flow travel of mean velocity and/or specific velocity. In non-contrast techniques, velocity measurements can be measured in at least two ways. In a first method, using diastolic-systolic subtraction imaging techniques, a displacement line can be drawn along the distance of MR signal displacement (by nearest point or line connected in length). The MRI display system may automatically record this as a distance and then, by clicking an appropriate button (e.g., or a right mouse click to select velocity), calculation of dividing such a distance by an appropriate corresponding time difference (e.g., between the effective elapsed times of the subtracted systolic and diastolic images) can be achieved. In a second method (e.g., ASL (arterial spin labeling) method), MRI signal produces a flow traveling from the start signal to the last signal in a distance divided by the (BBTI+TEeff) for Time-SLIP with FASE, (BBTI) for Time-SLIP with bSSFP in centric ordering, and (BBTI+ETL/2) for time-SLIP with bSSFP in sequential ordering).

The MRI system 100 according to the above-described exemplary embodiment will be described again. The MRI system 100 according to the exemplary embodiments includes a collecting unit, a specifying unit, an acquiring unit and a calculating unit. The collecting unit collects a plurality of fluid images that are images of the fluid traveling through the subject. The specifying unit specifies a distance traveled by the fluid by using difference images between a reference image that is one of the fluid images and each fluid image. The acquiring unit acquires an elapsed time corresponding to the traveled distance from pulse sequence information used to collect the fluid images. The calculating unit calculates a flow velocity by dividing the traveled distance by the elapsed time. For example, the MRI system controller 22 includes these units (not shown) and these units that the MRI system controller 22 includes controls the MRI sequence controller 30, the gantry 10, and other related components. Descriptions will be divided below for some cases. Specifically, descriptions will be provided for Case 1 where a plurality of fluid images at different cardiac phases are collected and Case 2 where a plurality of fluid images at different phases are collected by using Time-SLIP (time-spatial labeling inversion pulse) imaging method.

Some cases will be described below as exemplary embodiments. However, exemplary embodiments are not limited to the following cases.

[Case 1]

First, Case 1 will be described.

Figure 2:
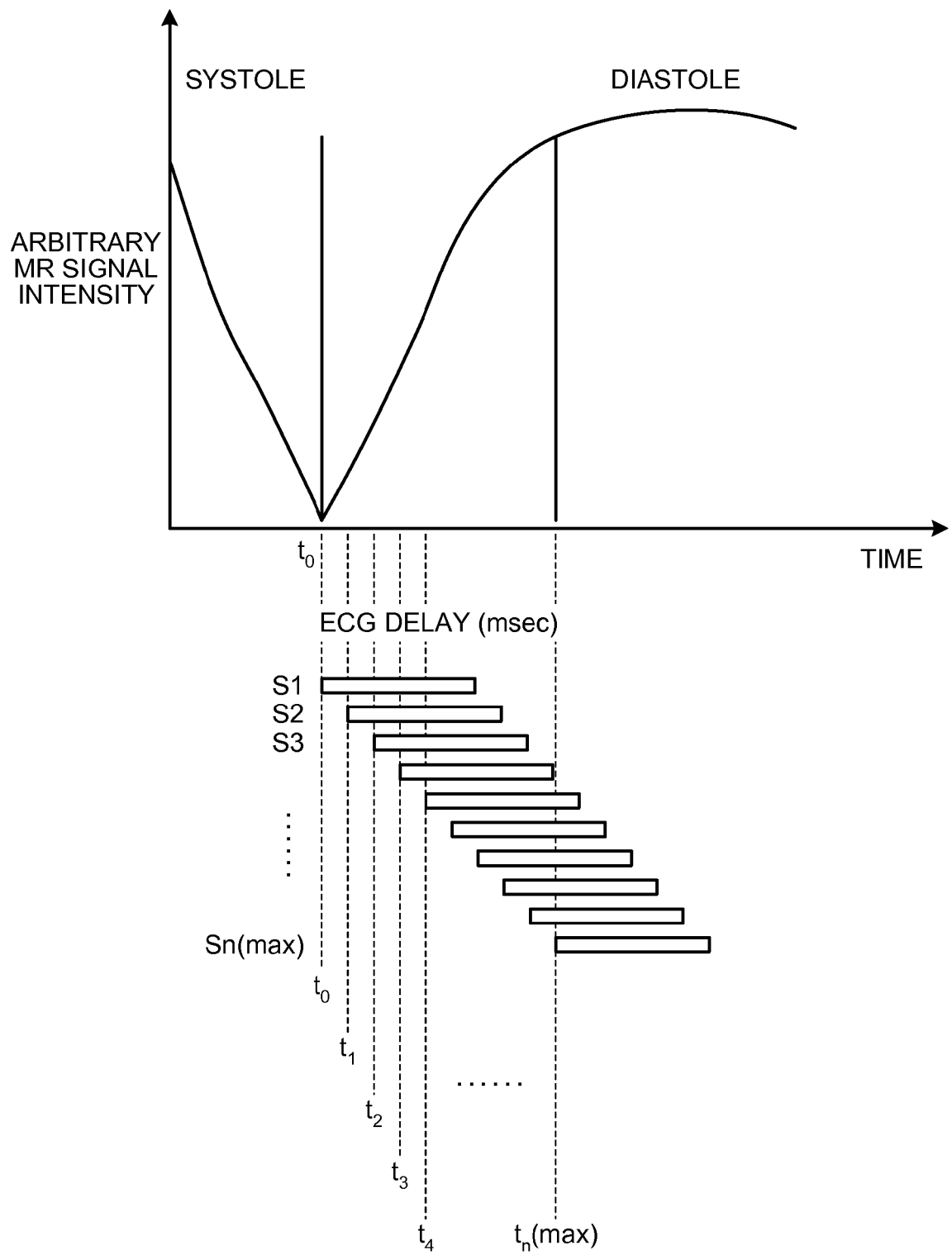
FIG. 2 is a timing diagram depicting successive cardiographic synchronization MR slice imaging sequences with respect to systole and diastole in an exemplary embodiment.

A FASE (fast asymmetric spin echo) (or FBI (fresh blood imaging)) sequence is used. If the phase-encode (PE) direction is perpendicular to the peripheral vessel flow, MR signal intensity of each FASE image with small increments therebetween (such as 1 RR to n RRs) will vary as shown in FIG. 2.

Figure 3:
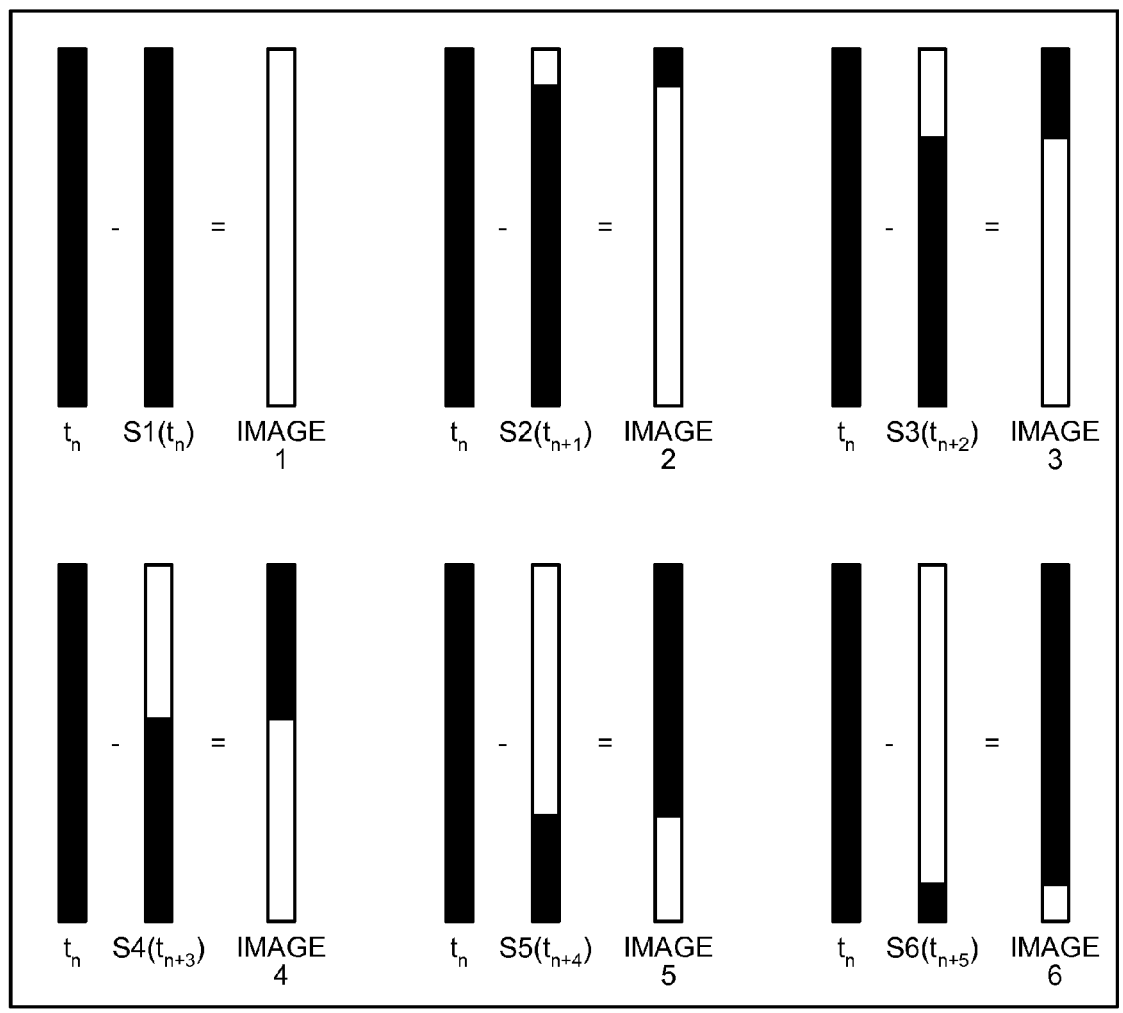
FIG. 3 is a schematic diagram depicting successive difference images obtained by the differences between a "dark (with low signal intensity)" systole image and "bright (with high signal intensity)" diastole images at successive cardiac-gated time increments as depicted in FIG. 2.

By Subtracting lower intensity signals (e.g., in a systole image) from higher intensity signals (e.g., at a diastolic-triggered image), a composite image of a flowing volume that appears like a moving object is obtained as shown in FIG. 3.

If displayed in cine, non-contrast time-resolved MRA can be seen. By tracking the MR flow signal along even tortuous vessels, a velocity is obtained from the travelled vessel length divided by the difference in time between images. A mean flow velocity (which can, of course, also be directly calculated if omission of calculating any intermediate specific velocity is required) can be obtained from the average of specific (incremental) flow velocities v1, v2, . . . vn.

The collecting unit according to Case 1 collects a plurality of fluid images of a fluid traveling through a subject at different cardiac phases. The specifying unit according to Case 1 specifies a distance traveled by the fluid by using the fluid images. The acquiring unit according to Case 1 acquires an elapsed time corresponding to the traveled distance from the pulse sequence information used to collect the fluid images. The calculating unit according to Case 1 calculates a velocity of the fluid by dividing the traveled distance by the elapsed time. For example, the MRI system controller 22 includes these units (not shown) and these units that the MRI system controller 22 includes control the MRI sequence controller 30, the gantry 10, and other related components.

The collecting unit collects the fluid images at different cardiac phases between diastole and systole by using, for example, an FBI imaging method. The FBI imaging method is a blood vessel imaging method using 3D FASE in which an appropriate delay from a synchronization signal (for example, R wave) is set and, by performing the collecting by using electrocardiographic synchronization or pulse synchronization, new blood pumped out of the heart is depicted. The intensity of the MR signal collected by the collecting unit varies between diastole and systole as depicted in FIG. 2. For this reason, the collecting unit collects the fluid images at different cardiac phases in a way that it sets delays $t_0$ msec, $t_1$ msec . . . , for which the delay from the electrocardiographic synchronization signal is gradually increases, and collects an MR signal $S_1$ in synchronization with a delay $t_0$ msec and collects an MR signal $S_2$ in synchronization with a delay $t_1$ msec.

Figure 4:
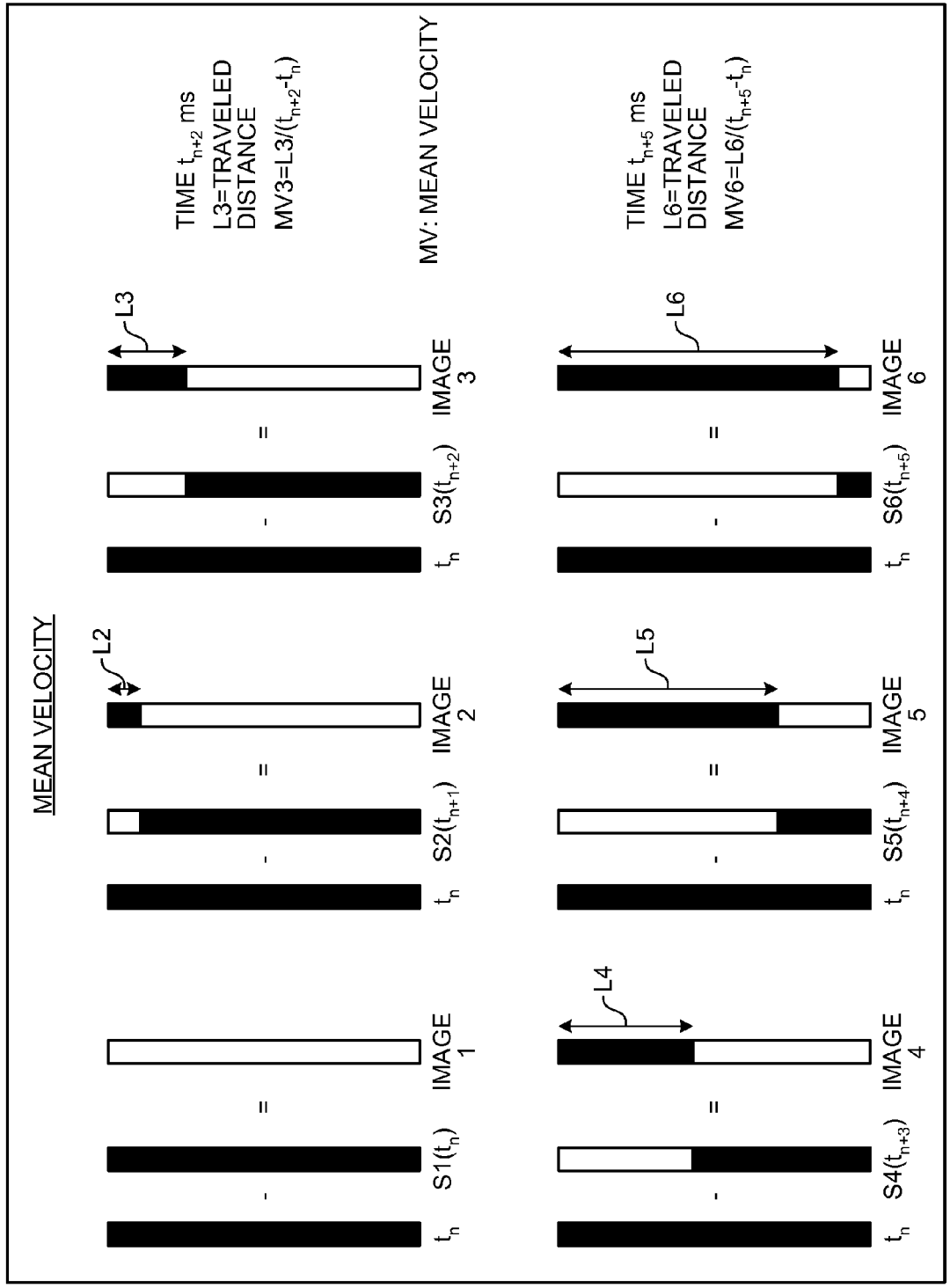
FIG. 4 is a schematic diagram similar to that of FIG. 3, but including annotations explaining how average or mean blood flow velocity can be calculated in accordance with an exemplary embodiment.

The specifying unit specifies the distance traveled by the fluid for each of the fluid images at different cardiac phases by using difference images between fluid images collected at predetermined cardiac phases and a fluid image collected at a reference cardiac phase. As described above, the MR signal intensity is different between the fluid images at different cardiac phases. Thus, for example, by subtracting a fluid image collected at a predetermined cardiac phase from the fluid image collected at the reference cardiac phase, the signal of the fluid (e.g., blood) traveling through the subject during that time can be depicted. For example, in FIG. 3, "$t_n$" denotes the reference cardiac phase and "S1 ($t_n$)" denotes the MR signal collected at the cardiac phase $t_n$. As shown in FIG. 3, for example, because the MR signal of the blood pumped out of the heart during systole has a low intensity (expressed by, for example, white in FIG. 3), the low-intensity portion gradually increases as the delay increases. Images 1 to 6 are images, each of which is obtained by subtracting the fluid image at each phase from the fluid image at the reference cardiac phase and subtracting information excluding blood, and each of which depicts blood. The specifying unit specifies the distance traveled by the fluid at each cardiac phase by analyzing Images 1 to 6, which are the difference images, and by discriminating, for example, the high-intensity part and the low-intensity part. For example, the specifying unit specifies the traveled distances L2 to L6 as shown in FIG. 4.

The acquiring unit acquires an elapsed time from the pulse sequence information for each traveled distance of each fluid image. For example, in Case 1, the elapsed time corresponding to each cardiac phase corresponds to a delay that is set as pulse sequence information. For this reason, the acquiring unit acquires the delay that is set as the pulse sequence information. For example, the acquiring unit acquires $t_{n+1}$ msec, $t_{n+2}$ msec, $t_{n+3}$ msec, $t_{n+4}$ msec and $t_{n+5}$ msec as delays.

Figure 5:
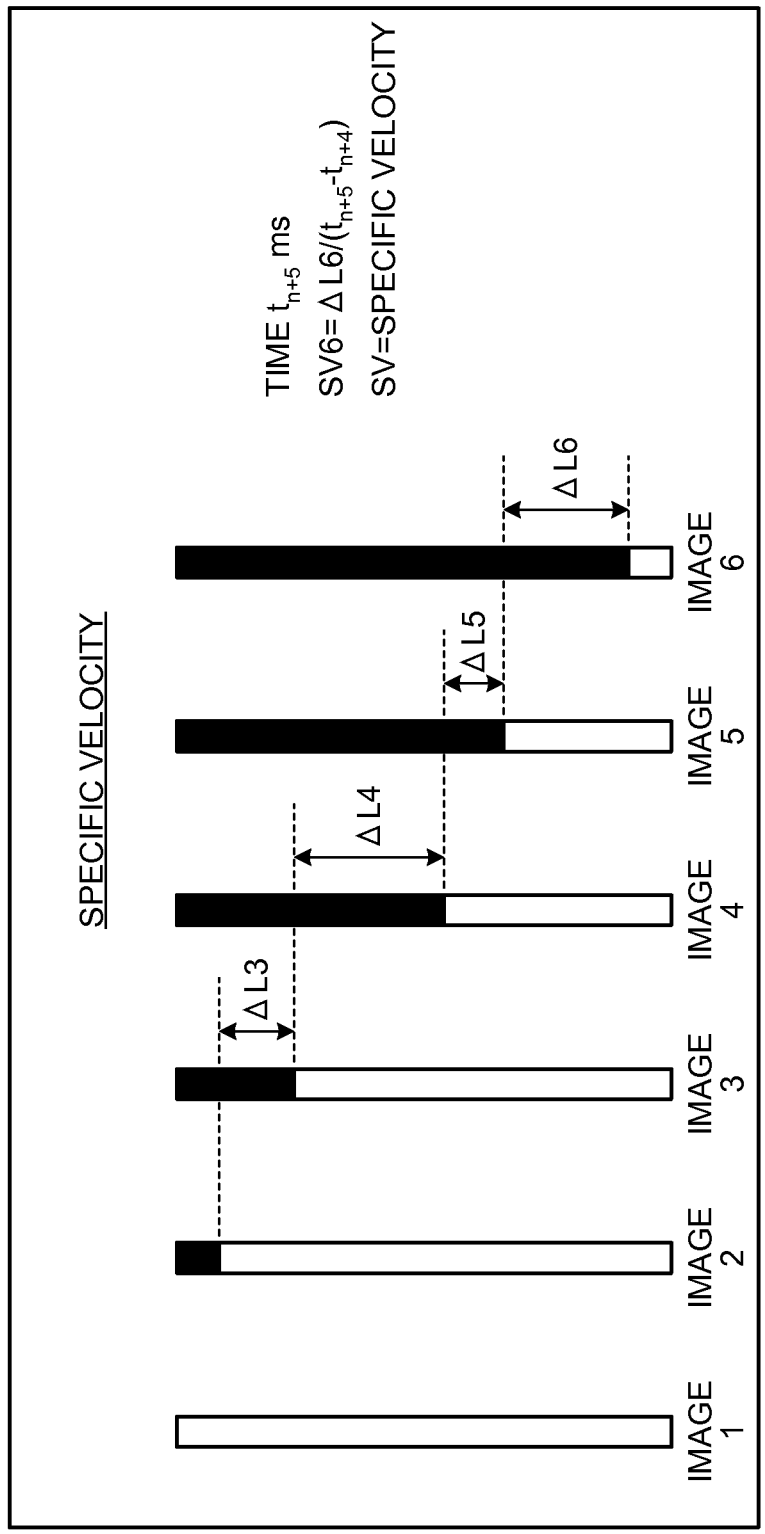
FIG. 5 is a similar schematic diagram showing the images different from those of FIGS. 3 and 4, but now with annotations depicting how specific velocity can be calculated at each successive time interval in accordance with an exemplary embodiment.
Figure 6:
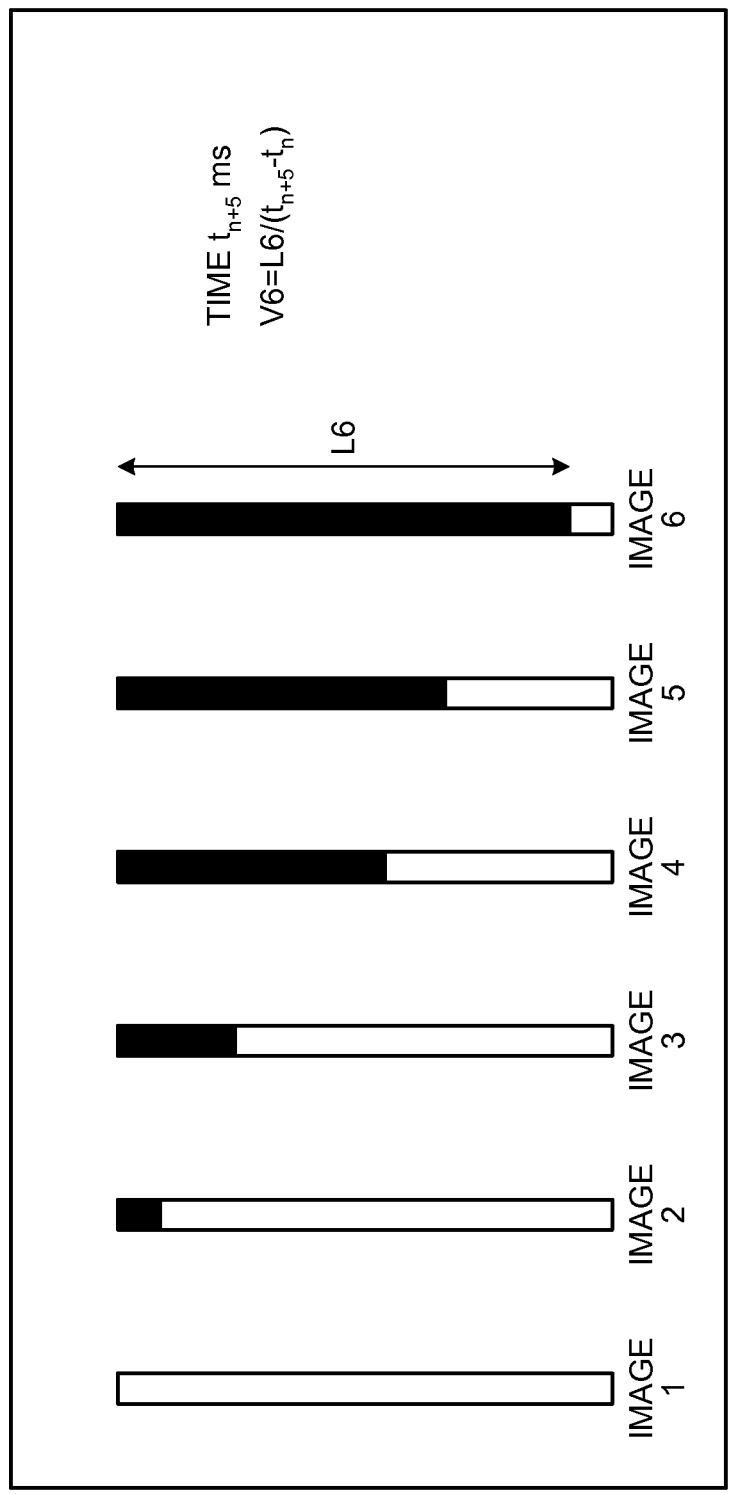
FIG. 6 is similar to FIG. 5, but now demonstrating how an overall mean or average velocity can be calculated over the entire sequence of difference images in an exemplary embodiment.

The calculating unit calculates a flow velocity by, for example, using each traveled distance and each elapsed time. For example, the calculating unit calculates a flow velocity by dividing an accumulated traveled distance obtained by accumulating each traveled distance by an accumulated elapsed time obtained by accumulating each elapsed time. For example, as shown in FIG. 6, the calculating unit calculates a velocity by dividing an accumulated traveled distance L6, which is obtained by accumulation at each cardiac phase, by an accumulated elapsed time ($t_{n+5}-t_n$). The method of calculating a velocity is not limited to this. The calculating unit may calculate a specific velocity specific to the cardiac phase by dividing a certain traveled distance by an elapsed time corresponding to the traveled distance. For example, as shown in FIG. 4, the calculating unit calculates a mean velocity MV3 by dividing a traveled distance L3 by an elapsed time ($t_{n+2}-t_n$). For example, as shown in FIG. 5, the calculating unit calculates a specific velocity SV by dividing a traveled distance $\Delta$L6, which represents a difference between Image 6 and Image 5, by an elapsed time ($t_{n+5}-t_{n+4}$).

[Case 2]

Case 2 will be described.

Flow-out (non-selective and selective pulses) or flow-in (only selective pulse) Time-SLIP, as well as alternative acquisition and subtraction (tag-on and off subtraction) also allows measurement of mean velocity.

When a single shot FSE (FASE) is used, a velocity can be calculated using a traveling flow volume within the BBTI time (tag to acquisition pulse) serving as a flow travel time and an effective TE (TEeff). Therefore, a velocity can be calculated as a length (L) of the traveling flow divided by (BBTI+TEeff).

When a bSSFP is used, a velocity can be calculated using a traveling flow within the BBTI time (tag to acquisition pulse) serving as the flow travel time. Therefore, a velocity can be calculated as a length (L) of the traveling flow divided by BBTI.

The collecting unit according to Case 2 collects a plurality of fluid images, which are images of a fluid flowing through a subject, at different phases by performing imaging in which a spin of the fluid is labeled and then echo signals of the spin are received after a predetermine time has elapsed for a plurality of times in which the predetermined time is changed. The specifying unit according to Case 2 specifies the distance traveled by the fluid by using the fluid images. The acquiring unit according to Case 2 acquires the elapsed time corresponding to the traveled distance from the pulse sequence information used to collect the fluid images. The calculating unit according to Case 2 calculates the flow velocity of the fluid by dividing the traveled distance by the elapsed time. For example, the MRI system controller 22 includes these units (not shown) and these units that the MRI system controller 22 includes control the MRI sequence controller 30, the gantry 10, and other related components.

In Case 2, the collecting unit collects a plurality of fluid images at different phases by using, for example, the Time-SLIP imaging method. The Time-slip imaging method is an imaging method of depicting a fluid flowing into or flowing out of an imaging area by labeling the fluid in positions independent of the imaging area and increasing or reducing the signal value of the fluid flowing into or flowing out of the imaging area. In the Time-SLIP imaging method, Time-SLIP pulses are applied after a predetermined wait time from the synchronization signal (e.g., R wave). The Time-SLIP pulses include an area non-selective inversion pulse ("non-selective pulse" in FIG. 7) and an area selective inversion pulse ("selective pulse" in FIG. 7) and on or off can be set for the area non-selective inversion pulse. When the fluid flowing into (or flowing out of) the imaging area is labeled by using the area selective inversion pulse, the intensity of the signal of the part that the fluid has reached after BBTI (black-blood time to inversion) time increases (decreases when the area non-selective inversion pulse is off). For this reason, the collecting unit sets a plurality of BBTI times and collects a plurality of fluid images at different phases.

When a labeling position is set outside the imaging area, the labeled fluid flows into the imaging area, which is referred to as "flow-in". In contrast, when a labeling position is set in the imaging area, the labeled fluid flows out of the imaging area, which is referred to as "flow-out". The exemplary embodiments can be applied to both "flow-in" and "flow-out".

The collecting unit according to Case 2 collects two fluid images by alternately repeating collecting in which labeling by using an area selective inversion pulse is performed and collecting in which labeling by using an area selective inversion pulse is not performed, for example, for each slice encode. In addition, the exemplary embodiments are also applicable to a case in which the collecting in which labeling is not performed is not performed for each slice encode, is performed, for example, once. Furthermore, the exemplary embodiments are also applicable to a case in which collecting in which no labeling is performed.

Figure 7:
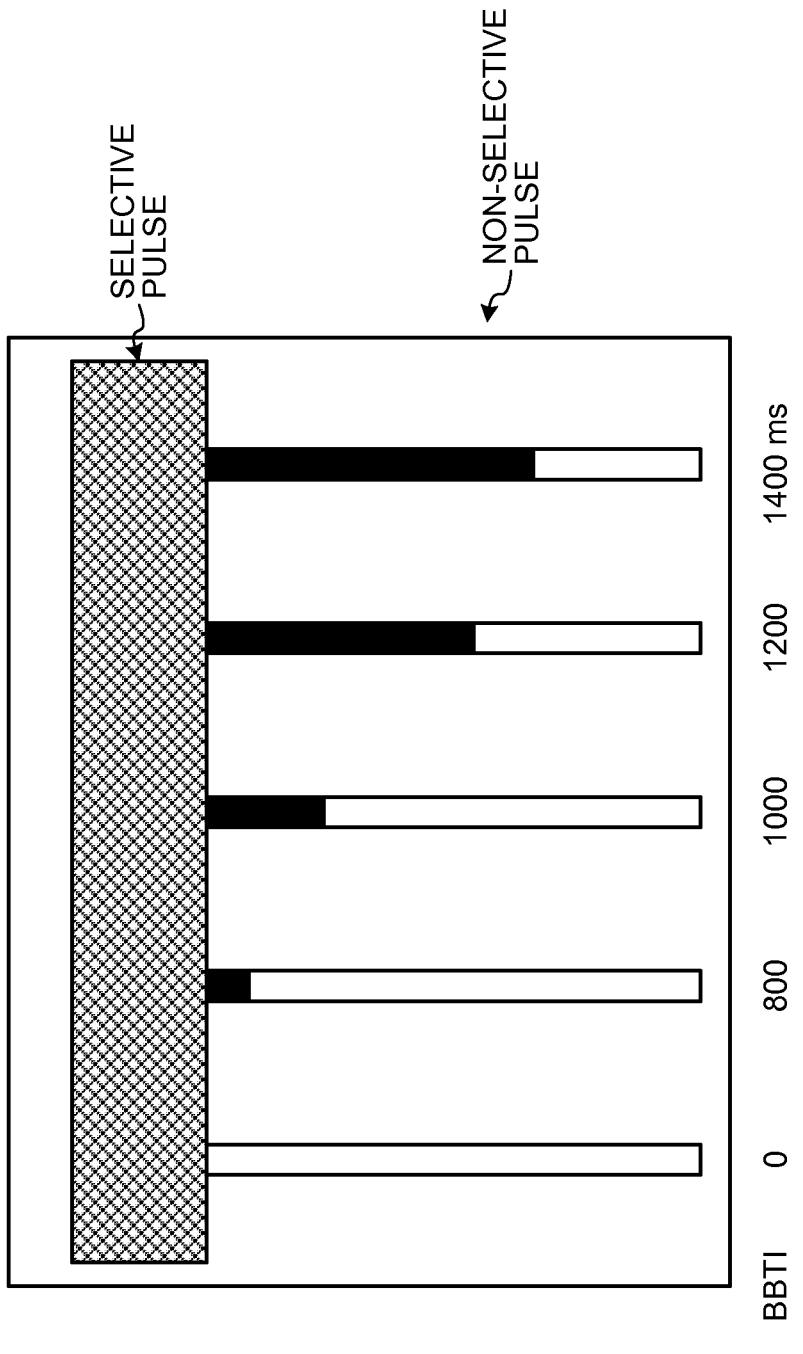
FIG. 7 schematically depicts velocity measurements in accordance with another exemplary embodiment using Time-SLIP (time-spatial labeling inversion pulse) imaging methods (flow-out and tag-on/tag-off subtraction methods).

The specifying unit according to Case 2 specifies the distance traveled by the fluid in each of the fluid images at different phases by using difference images between a reference image that is collected by imaging in which no labeling is performed and each fluid image collected by imaging in which labeling is performed. For example, the specifying unit extracts a labeled part by obtaining a difference between the two fluid images collected for the same slice encode and reduces the background signal. Alternatively, when collecting in which no labeling is performed is performed once, the specifying unit extracts only a labeled part by obtaining a difference between a reference image collected in the collecting once and each fluid image collected by imaging in which labeling is performed and reduces the background signal. As shown in FIG. 7, in a difference image, as an increase in the BBTI time becomes greater, the high-intensity part gradually increases (for example, expressed by black in FIG. 7). The specifying unit specifies the traveled distance of the fluid at each phase by analyzing the each fluid image on the basis of the intensity and, for example, distinguishing between the high intensity part and a low intensity part.

The acquiring unit acquires an elapsed time from pulse sequence information for each traveled distance of each fluid image. For example, in Case 2, the collecting unit assumes a case where a plurality of fluid images at different phases are collected by using the Time-Slip method using the FASE (fast asymmetric Spin Echo) method. In this case, the acquiring unit acquires, as an elapsed time, a value obtained by adding a BBTI time to an effective echo time (TEeff (effective time to echo)) from the pulse sequence information.

The acquiring unit according to Case 2 may acquire an elapsed time corresponding to a traveled distance in accordance with the method of filling a k space used to generate fluid images. A case is assumed in which the collecting unit collects a plurality of fluid images at different phases by using the Time-SLIP imaging method using the bSSFP (balanced steady state free precession) method. In this case, in a case of centric ordering in which phase encodes are arrayed from the center of the k space, the acquiring unit acquires, as an elapsed time, a BBTI time from the pulse sequence information. In contrast, in a case of sequential ordering in which phase encodes are sequentially arrayed in the k space, the acquiring unit acquires a value obtained by adding a BBTI time to a time corresponding to half of the phase encode number. These elapsed times are designed to correspond to the elapsed times in which MR signals with which the center part of the k space is filled are collected.

Like Case 1, for example, the calculating unit calculates a flow velocity by, for example, dividing an accumulated traveled distance obtained by accumulating each traveled distance by an accumulated time obtained by accumulating each elapsed time.

In Case 2, a pCASL (pulsed continuous arterial spin labeling) in which labeling pulses are continuously radiated may be used as a labeling method. Alternatively, instead of continuously radiating labeling pulses, the width or size of the labeling area (labeling area) may be set larger.

Preferably, regardless of whether in Case 1 or Case 2, all calculations are done on the MR image console by selecting an icon of "Velocity" ("mean velocity" and/or "specific velocity"), e.g., with a mouse click.

As those in the art will appreciate, the non-contrast Time-SLIP (ASL) technique observes flow fluids by using multiple different BBTI times in MRI sequences.

The exemplary embodiments provide a relatively simple GUI to facilitate velocity measurements (specific and/or mean) instead of requiring such to be calculated off-line using a calculation tool separate from the MRI display system. This GUI allows an easy and quick calculation of mean and/or specific flow velocities.

As depicted in FIG. 2, an FBI/Navi routine or the like may be utilized to obtain successive slice images S1, S2, S3 . . . at successively delayed times from systole to diastole in the typical PQRSTU cardiac cycle. One complete cardiac cycle is sometimes referred to as an "R-R" cycle. Of course, the frequency of R cardiac pulses equates to the subject's pulse rate.

The "FBI/Navi routine" is a feature of obtaining a delayed time appropriate for FBI imaging from the images collected by ECG-Prep imaging. ECG-Prep imaging is 2D FASE imaging that is performed in order to set a delayed time in the FBI imaging method prior to imaging by the FBI imaging method. By ECG-Prep imaging, a plurality of images at different cardiac phases are collected while the delayed time from the synchronization signal (e.g., R wave) is changed and the collected images or signal values analyzed on the basis of the images are displayed on the display. FBI-Navi extracts an area in which the signal value significantly changes by analyzing the images collected by ECG-Prep imaging, obtains signal value differences each between a reference image and each image, and displays the obtained signal value differences in a graph.

Using cardiac (or peripheral pulse) gating as appropriate, MRI sequences can be imposed on the subject at successively delayed points in the cardiac cycle. As measured from systole at $t_0$, the delay increments for each successive slice S1, S2, . . . Sn(max) are depicted in FIG. 2 out to a maximum time at tn(max).

As those in the art will appreciate, difference images can be generated by subtracting one of these images from other images on a pixel-by-pixel basis. To obtain the maximum contrast in MRA, typically the systole image having minimum signal intensity will be subtracted from the diastole image having the maximum signal intensity so as to produce a single MRA image.

However, if the successive images S2, S3, etc., are subtracted from the systole image S1, a succession of difference images will be produced which can depict a leading edge of a pulsatile fluid flow almost as an advancing "object" along a subject's artery.

FIG. 3 is a schematic depiction of an idealized entirely linear artery. The artery has been imaged at time $t_0$ at systole and then successively imaged again at incrementally increasing time intervals towards diastole at $t_{n+1}$, $t_{n+2}$, etc. The resulting sequence of images starts with a null Image 1 (since two identical images are being subtracted) and then progresses to reveal a flowing fluid in the imaged artery section starting from the top and progressing towards the bottom (in FIG. 3) as the flowing fluid produces ever-increasing MR signal intensity because the imaging times approach more closely to diastole. In effect, one can discern a leading edge of flowing fluid starting from time $t_n$ and traversing various lengths of the artery segment through the different successive time intervals involved.

Thus, as depicted in FIG. 4, it is possible to measure the total length of distance travelled by the flowing fluid at the end of each successive time interval and to divide that total length by the elapsed time so as to provide a mean velocity measurement at the end of each image interval.

Alternatively, as depicted in FIG. 5, a specific velocity for each incremental time interval between images can also be calculated by calculating the incremental distance travelled between images and dividing by the appropriate related time interval. Assuming that the time interval between images is equal, it will thus be seen in FIG. 5 that the specific velocity increases at Image 3 compared to Image 2, and again at Image 4 compared to Image 3. However, it appears to decrease at Image 5 compared to Image 4 and then to increase again at Image 6 compared to Image 5.

As depicted in FIG. 6, the same set of successive Images 1 to 6 can also be analyzed so as to calculate only the average or mean velocity over the entire interval (comparing Image 6 to Image 1).

In effect, as displayed in cine mode, using diastolic-systolic images, non-contrast time-resolved MRA can now include flow velocity measurements. By tracking the flowing signal source, even along tortuous vessels, the length of the vessel segment travelled and divided by the time required for such travel gives a velocity (either average or mean velocity over a succession of intervals and/or a succession of specific velocities if measured between intervals or smaller groups of intervals). That is, the average of the incremental specific velocities from one period to the next gives a mean or average velocity over the longer time period encompassing all of the images.

FIG. 7 schematically depicts Time-SLIP non-contrast imaging of fluid flows. The selective and non-selective pulses are represented by differently sized rectangles. As those in the art will appreciate, by using different BBTI intervals, one can achieve successive images of fluid flows within arteries, veins, etc., similar to the successive images at different time increments described in earlier figures for diastolic-systolic difference images. As should be apparent, measurement of travelled distances along arteries, veins, etc., and dividing by the associated travel times can also produce velocity measurements using this non-contrast flow imaging technique.

Figure 8:
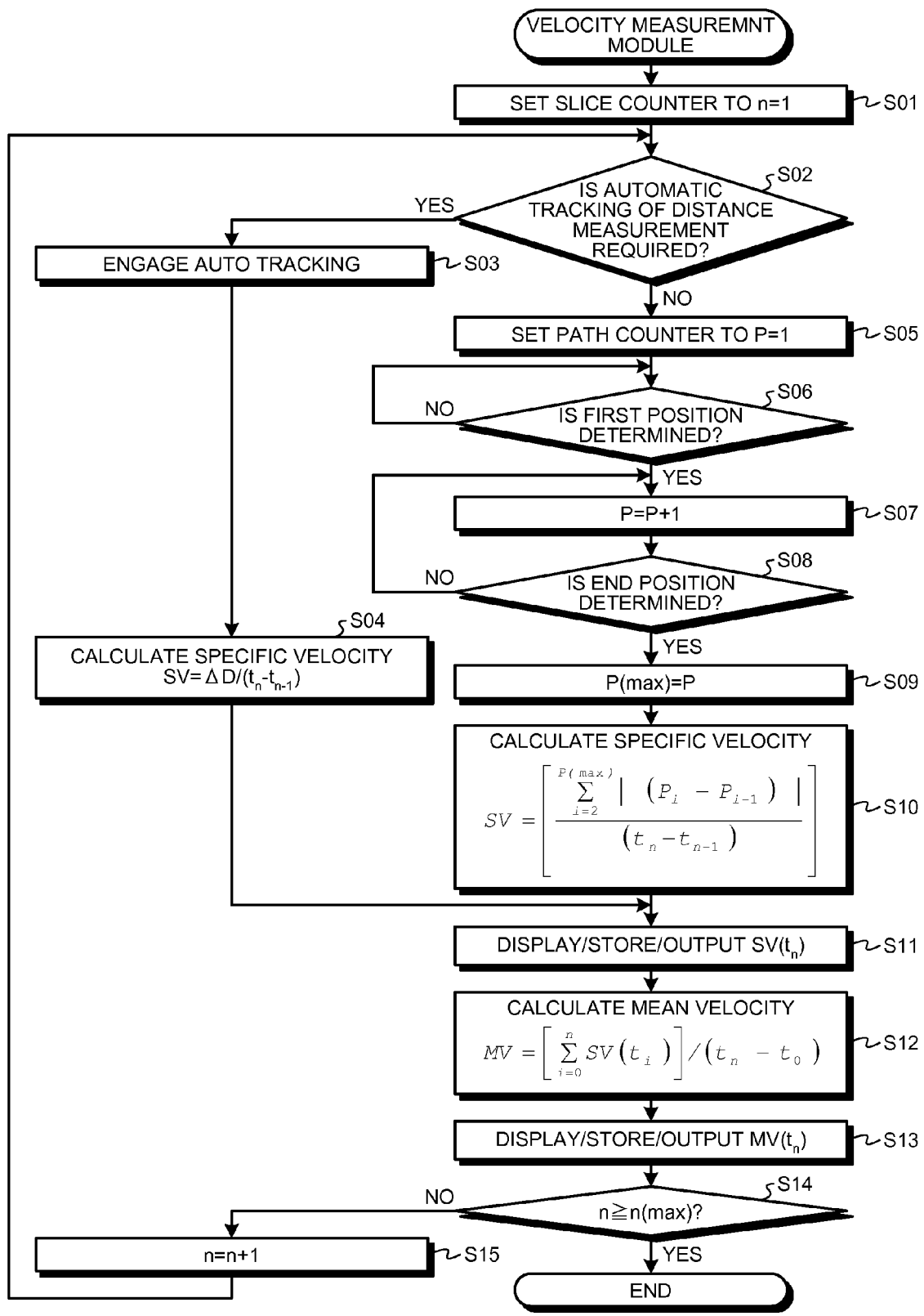
FIG. 8 is a schematic flow chart for an exemplary computer program code structure that may be utilized in an exemplary embodiment.

FIG. 8 schematically depicts a velocity measurement module of computer program code structure. The module may be entered by any suitable means (e.g., by an operator using mouse clicks on a suitably displayed icon or menu, finger-actuated inputs on a touch-sensitive screen, keyboard inputs, etc.) associated with a main or supervisory operating system or the like.

At step S01, a slice counter n is initialized with a value of 1. At step S02, a test is made to see whether an option has been set for system auto-track of distance measurements (e.g., by setting a control parameter in a basic setting dialog or the like to use an automatic machine-implemented distance tracking algorithm). If so, then the auto-track feature is engaged at step S03 and a specific velocity SV is calculated between slices taken at $t_{n-1}$ and subsequent $t_n$ at step S04.

Figure 9:
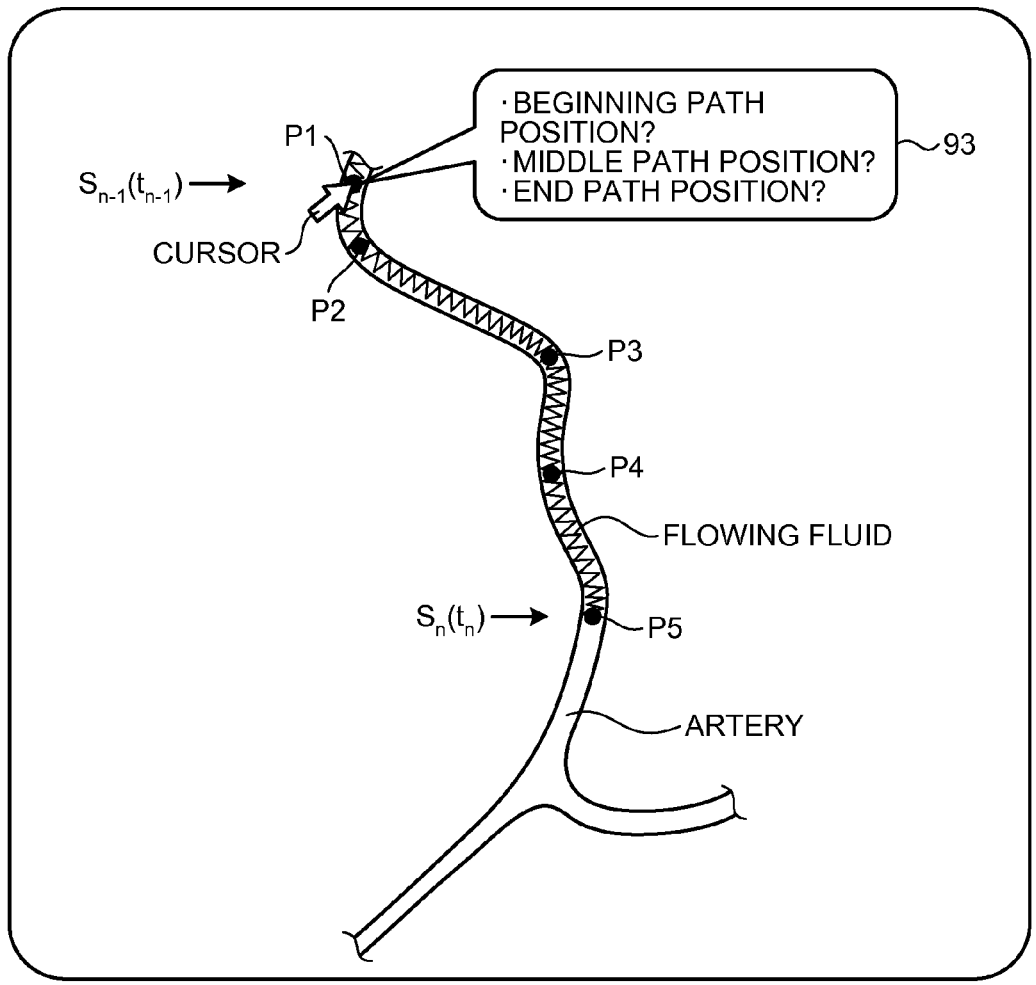
FIG. 9 is a schematic depiction of a operator screen utilized when the operator defines successive path position points for blood flow along a tortuous path between two successive imaging times.

If the auto-track feature is not desired, then at step S05, the path counter p is initialized at a value of 1. Thereafter, at step S06, a wait loop is executed for the operator to define a first position. For example, as shown at FIG. 9, the operator may move a curser onto the first point P1 (associated with imaging time $t_{n-1}$) and click a predetermined mouse button so as to define a first position on a displayed image of fluid flow in an artery or the like. A pop-up menu 93 may also be provided giving the operator a choice of identifying a particular defined point as being an initial path position, an intermediate path position, or an end path position. As depicted, for example, in FIG. 9, because operator-defined points P1 to P5 have been defined at strategic points along a tortuously curved vessel (between imaging times $t_{n-1}$ and $t_n$), straight line segments between the clear points along the path of flow closely approximate the distance of flow from slice image Sn−1 to slice image Sn. Once a first position has been defined at step S06 (in FIG. 8), the path counter P is incremented at step S07 as shown in FIG. 8. Thereafter, a wait loop is executed as additional positions along the path are defined by the operator and the path counter is incremented until an end position has been defined (step S08). At that point, the maximum value for the path parameter P(max) is defined at step S09 as the current value of the path counter. The specific velocity SV is then calculated at step S10 for that increment of flow between successive slice images Sn and Sn−1.

At step S11, the specific velocity SV (no matter how calculated) associated with the ending time $t_n$ is then displayed, stored or otherwise output (e.g., to a remote site as may be desired and configured in a preference section of the system). A travel mean velocity MV is then calculated at step S12 and, at step S13, is similarly displayed, stored or otherwise output as may be desired (e.g., as configured before in the system). At step S14, a test is made to see if the slice counter has yet reached the end value (i.e., slice Sn(max)). If not, then the slice counter is incremented at step S15 and control is passed back either to the decision step S02 as depicted in FIG. 8 or directly to a re-initialization of the path counter at step S06 (i.e., if desiring the operator not to operate the auto-track system). When all of the available slice data has been processed, then exit of this module is taken as depicted in FIG. 8.

Figure 10:
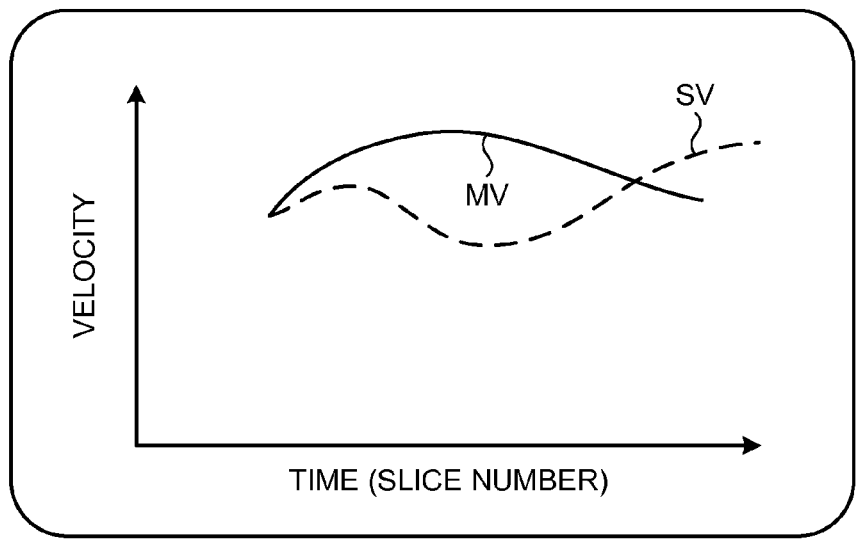
FIG. 10 is a schematic depiction of a possible output display graph of specific velocity and/or mean velocity versus time and/or slice position according to the exemplary embodiment.

As depicted in FIG. 10, the specific velocity SV and/or travel mean velocity MV may be graphically displayed as a function of time (or slice number or the like).

[Display]

The MRI system 100 according to the exemplary embodiments may further include a display controller that displays information including the velocity on the display in at least one of the fluid images and the reference image for which a difference process with respect to the fluid images is performed. For example, the MRI system controller 22 includes the display controller (not shown) and the display controller that the MRI system controller 22 includes controls the related components. In the exemplary embodiments, the fluid images collected by the collecting unit are fluid images collected by, for example, the FBI imaging method or fluid images collected by the Time-SLIP imaging method, which are images with high resolution. Because the MRI system 100 according to the exemplary embodiments calculates "velocity of fluid" as functional information from these high-resolution morphological images, the morphological images coincide with the source of calculation of function information.

For example, while displaying the morphological images, the display controller may display and superpose information on the fluid velocity on the morphological images. For example, the display controller may perform displaying (e.g., filling the blood vessels of the lower limbs) to represent that there is a velocity in a part where a velocity exists, or displaying (e.g., hatching the blood vessels of the lower limbs) to represent that there is no velocity in a part where no velocity exists, on the morphological images in which vessels of the lower extremity are depicted. Furthermore, for example, while displaying 3D morphological images, the display controller may display and superpose 2D fluid video data on the 3D morphological images (for example, Images 1 to 6 illustrated in FIG. 3 are successively played).

According to the magnetic resonance imaging apparatus and magnetic resonance imaging method according to at least one of the exemplary embodiments, the velocity of the fluid can be obtained.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) apparatus comprising
MRI gantry components including static and gradient magnetic field generators, at least one radio frequency (RF) coil coupled to an imaging volume, at least one RF transmitter, at least one RF receiver and at least one control computer having a processor and memory configured to control said gantry components so as to effect operations including:
collecting a plurality of fluid images that are MR images of a fluid traveling through a subject, each of said MR images having been acquired by execution of an MRI pulse sequence at a different cardiac phase;
specifying a traveled distance of the fluid between different cardiac phases by using a difference image between a reference image that is one of the fluid images and each other fluid image;
acquiring an elapsed time corresponding to the traveled distance of the fluid between different cardiac phases based on MRI pulse sequence information that was used to collect the fluid images at said different cardiac phases; and
calculating a flow velocity of the fluid for each said different cardiac phase by dividing the traveled distance by the elapsed time for each said different cardiac phase,
wherein the elapsed time is an elapsed time in which MR signals with which the center part of a k space is filled are collected.

2. The magnetic resonance imaging apparatus according to claim 1, wherein the processor is configured to control said gantry components so as to effect further operations including displaying information including the specific flow velocities on a display concurrent with display of at least one of the fluid images and the reference image for which a difference process with respect to the fluid images has been performed.

3. The magnetic resonance imaging apparatus according to claim 1, wherein the traveled distance for each of said different cardiac phases is operator-specified by displaying a fluid image on a display and accepting an operator designation of a position in the displayed fluid image to which the fluid has reached.

4. The magnetic resonance imaging apparatus according to claim 1, wherein the traveled distances are operator specified by an operator analyzing a displayed fluid image and designating said different cardiac phases corresponding to specified points along a path which the fluid has traveled.

5. A magnetic resonance imaging (MRI) comprising
MRI gantry components including static and gradient magnetic field generators, at least one radio frequency (RF) coil coupled to an imaging volume, at least one RF transmitter, at least one RF receiver and at least one control computer having a processor and memory configured to control said gantry components so as to effect operations including:
collecting a plurality of fluid images that are images of a fluid traveling through a subject;

specifying a traveled distance of the fluid by using a difference image between a reference image that is one of the fluid images and each other fluid image;

acquiring an elapsed time corresponding to the traveled distance from pulse sequence information that is used to collect the fluid images; and calculating a flow velocity of the fluid by dividing the traveled distance by the elapsed time, wherein the elapsed time is an elapsed time in which MR signals with which the center part of a k space is filled are collected, and wherein (a) in a case of centric ordering in which phase encodes are arrayed from the center of the k space, a BBTI (black-blood time to inversion) time is acquired as the elapsed time from the pulse sequence information and (b) in a case of sequential ordering in which phase encodes are sequentially arrayed in the k space, a value obtained from the pulse sequence information by adding the BBTI time to a time corresponding to half of a phase encode number is acquired as the elapsed time.

6. A magnetic resonance imaging (MRI) apparatus comprising

MRI gantry components including static and gradient magnetic field generators, at least one radio frequency (RF) coil coupled to an imaging volume, at least one RF transmitter, at least one RF receiver and at least one control computer having a processor and memory configured to control said gantry components so as to effect operations including:

collecting a plurality of fluid images at different cardiac phases, wherein the collecting includes collecting a first fluid image at systole in a cardiac cycle and successively collecting a plurality of second fluid images at time intervals that incrementally increase from the systole towards diastole in the cardiac cycle;

specifying a traveled distance of the fluid in each second fluid image by using a difference image between the first fluid image and the second fluid image;

acquiring an elapsed time corresponding to the traveled distance in each second fluid image from pulse sequence information that is used to collect the second fluid image; and calculating a flow velocity by dividing an accumulated traveled distance obtained by accumulating each traveled distance by an accumulated elapsed time obtained by accumulating each elapsed time.

7. The magnetic resonance imaging apparatus according to claim 6, wherein the processor is configured to control said gantry components so as to effect further operations including displaying information including the flow velocity on a display in at least one of the second fluid images and the first image for which a difference process with respect to the fluid images is performed.

8. The magnetic resonance imaging apparatus according to claim 6, wherein the traveled distance is specified by displaying a fluid image on a display and accepting a designation of a position that the fluid has reached.

9. The magnetic resonance imaging apparatus according to claim 6, wherein the traveled distance is specified by analyzing the image and tracking a path along which the fluid travels.

10. A magnetic resonance imaging (MRI) apparatus comprising

MRI gantry components including static and gradient magnetic field generators, at least one radio frequency (RF) coil coupled to an imaging volume, at least one RF transmitter, at least one RF receiver and at least one control computer having a processor and memory configured to control said gantry components so as to effect operations including:

collecting a plurality of fluid images that are images of a fluid traveling through a subject, wherein a first fluid image is collected by performing imaging in which a spin of the fluid is not labeled and a plurality of second fluid images are collected by performing imaging in which a spin of the fluid is labeled and then echo signals of the spin are received after a time interval has elapsed for a plurality of times while changing the time interval for respective ones of the plurality of times;

specifying a traveled distance of the fluid in each second fluid image by using a difference image between the first fluid image and the second fluid image;

acquiring an elapsed time corresponding to the traveled distance in each second fluid image from pulse sequence information that is used to collect the second fluid image, and calculating the flow velocity by dividing an accumulated traveled distance obtained by accumulating each traveled distance by an accumulated elapsed time obtained by accumulating each elapsed time.

11. The magnetic resonance imaging apparatus according to claim 10, wherein the plurality of fluid images are collected at different phases by using a Time-SLIP (time-sequential labeling inversion pulse) imaging method.

12. The magnetic resonance imaging apparatus according to claim 10, wherein the plurality of fluid images are collected at different phases by using a Time-SLIP imaging method using a FASE (fast asymmetric spin echo) method, and the elapsed time is acquired as a value obtained from the pulse sequence information by adding a BBTI time to an effective time to echo (TEeff).

13. The magnetic resonance imaging apparatus according to claim 10, wherein the processor is configured to control said gantry components so as to effect further operations including displaying information including the flow velocity on a display in at least one of the second fluid images and the first image for which a difference process with respect to the fluid images is performed.

14. The magnetic resonance imaging apparatus according to claim 10, wherein the traveled distance is specified by displaying a fluid image on a display and accepting a designation of a position that the fluid has reached.

15. The magnetic resonance imaging apparatus according to claim 10, wherein the traveled distance is specified by analyzing the image and tracking a path along which the fluid travels.

* * * * *